United States Patent
Wang et al.

(10) Patent No.: US 10,144,945 B2
(45) Date of Patent: *Dec. 4, 2018

(54) LAYERED MICROFLUIDIC LIVING CELL ARRAY

(71) Applicants: Research Foundation of the City University of New York, New York, NY (US); Memorial Sloan Kettering Cancer Center, New York, NY (US)

(72) Inventors: Sihong Wang, Scarsdale, NY (US); Zeynep Dereli-Korkut, North Bergen, NJ (US); Xuejun Jiang, Cresskill, NJ (US)

(73) Assignees: Research Foundation of the City University of New York, New York, NY (US); Memorial Sloan Kettering Cancer Center, New York, NY (US)

( * ) Notice: Subject to any disclaimer, the term of this patent is extended or adjusted under 35 U.S.C. 154(b) by 674 days.

This patent is subject to a terminal disclaimer.

(21) Appl. No.: 14/257,182

(22) Filed: Apr. 21, 2014

(65) Prior Publication Data

US 2014/0228250 A1    Aug. 14, 2014

Related U.S. Application Data

(63) Continuation of application No. PCT/US2012/061229, filed on Oct. 20, 2012.

(60) Provisional application No. 61/549,322, filed on Oct. 20, 2011.

(51) Int. Cl.
| | |
|---|---|
| C12Q 1/00 | (2006.01) |
| C40B 60/00 | (2006.01) |
| C12M 3/06 | (2006.01) |
| C12N 5/00 | (2006.01) |
| C12N 5/09 | (2010.01) |
| C40B 40/00 | (2006.01) |

(52) U.S. Cl.
CPC ............ *C12Q 1/00* (2013.01); *C12M 23/16* (2013.01); *C12N 5/0068* (2013.01); *C12N 5/0693* (2013.01)

(58) Field of Classification Search
CPC ........................................................ C12Q 1/00
USPC ............................................................ 506/14
See application file for complete search history.

(56) References Cited

U.S. PATENT DOCUMENTS

| | | | |
|---|---|---|---|
| 2010/0120077 A1 | 5/2010 | Daridon | |
| 2010/0323447 A1* | 12/2010 | Takayama | B01L 3/50273 435/383 |
| 2011/0004304 A1* | 1/2011 | Tao | C12M 23/16 623/6.63 |
| 2011/0082563 A1* | 4/2011 | Charest | A61F 2/022 623/23.65 |
| 2014/0273223 A1* | 9/2014 | Cho | C12M 23/16 435/396 |

FOREIGN PATENT DOCUMENTS

| | | | | |
|---|---|---|---|---|
| CN | 101649290 | | 5/2012 | |
| GB | WO 2010013016 A2 | * | 2/2010 | ............ B01L 3/5025 |
| WO | WO2001019505 B1 | | 3/2001 | |
| WO | WO2010013016 A2 | | 2/2010 | |
| WO | WO2011014674 A2 | | 2/2011 | |

OTHER PUBLICATIONS

Liu et al., A 3-D Microfluidic Combinatorial Cell Array, Biomed Microdevices, 2010, 13, 191-201.*
International Search Authority (ISA/US); International Search Report dated Jan. 18, 2013 for PCT/US12/61229, 2 pgs.
Zhang et al.; Self-Complementary Oligopeptide Matrices support mammalian cell attachment; Biomaterials 16 (1995) pp. 1385-1393 (total 8 pgs.).
Zhang et al.; Spontaneous assembly of a self-complementary oligopeptide to form a stable microscopic membrane; Proc. Natl. Acad. Sci USA, vol. 90, Apr. 1993; pp. 3334-3338 (total 5 pgs.).
King et al.; A high-throughput microfluidic real-time gene expression living cell array; Lab Chip; Jan. 2007; 7(1): pp. 77-85 (total 9 pgs.).
Gurski et al.; 3D Matrices for Anti-Cancer Drug Testing and Development; Oncology Issues Jan./Feb. 2010, pp. 20-25 (total 6 pgs.).
Dereli-Korkut, Z. et al.; Three Dimensional Microfluidic Cell Arrays for ex Vivo Drug Screening with Mimicked Vascular Flow; Analytical Chemistry; Feb. 25, 2014; pp. 2997-3004; vol. 89; 2014 American Chemical Society.

* cited by examiner

*Primary Examiner* — Amy M Bunker
(74) *Attorney, Agent, or Firm* — Peter J. Mikesell; Schmeiser, Olsen & Watts, LLP (57) ABSTRACT

A layered, microfluidic living cell array is disclosed. The cell array comprises a first layer comprising at least one cell culture channel; a second layer comprising at least one microfluidic channel; and a third layer, disposed between the first layer and the second layer. The third layer comprises a filter membrane with a plurality of pores, each pore fluidly connecting the microfluidic channel to the cell culture channel.

12 Claims, 9 Drawing Sheets

LAYERED MICROFLUIDIC LIVING CELL ARRAY

CROSS-REFERENCE TO RELATED APPLICATIONS

This application is a continuation of international application number PCT/US2012/061229 (filed Oct. 20, 2012) which claims priority to and the benefit of U.S. provisional patent application Ser. No. 61/549,322 filed Oct. 20, 2011, which applications are incorporated herein by reference in their entirety.

STATEMENT REGARDING FEDERALLY FUNDED RESEARCH OR DEVELOPMENT

This invention was made with government support under contract no. 1U54CA137788-01 awarded by the National Institute of Health (NIH) and the National Cancer Institute (NCI) and under contract no. 1055608 by the National Science Foundation (NSF) and the Center of Bioscience Education & Technology (CBET). The government has certain rights in the invention.

FIELD OF THE INVENTION

This invention relates, in one embodiment, to a three dimensional microfluidic cell array that functions as a scaffold for growing cells.

BACKGROUND

The promise of improved cancer therapy has been one of the driving forces for cell death research over the past decade. There is growing evidence that many of the molecular and cellular changes that occur in cancer development diminish the ability of cells to undergo apoptosis and that resistance to apoptosis causes drug resistance. On the other hand, many studies have demonstrated that apoptosis is a frequent outcome of effective anticancer therapy. Therefore, developing and screening novel anticancer drugs that target apoptosis pathways have received increasing attention in the past few years. Identification of novel compounds and drug targets involved in apoptosis regulation is still a major roadblock to anticancer drug development due to the lack of a high throughput apoptotic screening system which can systematically measure dynamic expression of multiple proteins and genes as well as enzyme activities in real time in intact cells from multiple stimuli.

Cell cultures are often grown in the lab to assist in measuring the effectiveness of an anticancer drug. For example, colonies of cancer cells can be grown from cells that were removed from a patient. A variety of drugs may be tested for activity against these particular cancer cells. Conventionally, these colonies are grown in suspension or in two-dimensional arrays. This environment does not adequately mimic the native environment of the cancer cell when it was within the patient. This environmental change can impose phenotypic changes in the resulting colony of cancer cells that may, in some instances, alter the responsiveness of the colony to anti-cancer agents.

Some attempts have been made to produced three-dimensional cell arrays but these have not proven entirely satisfactory. Therefore, an improved device and method for growing cells is desired.

SUMMARY OF THE INVENTION

In one embodiment, a layered, microfluidic living cell array is disclosed. The cell array comprises a first layer comprising at least one cell culture channel; a second layer comprising at least one microfluidic channel; and a third layer, disposed between the first layer and the second layer. The third layer comprises a filter membrane with a plurality of pores, each pore fluidly connecting the microfluidic channel to the cell culture channel.

An advantage that may be realized in the practice of some disclosed embodiments of the cell array is that the native environment experienced by a cell is more closely approximated.

BRIEF DESCRIPTION OF THE DRAWINGS

The present invention is disclosed with reference to the accompanying drawings, wherein:

FIG. 3A is a bisected profile of an exemplary cell array showing fluid flow paths while

Corresponding reference characters indicate corresponding parts throughout the several views. The examples set out herein illustrate several embodiments of the invention but should not be construed as limiting the scope of the invention in any manner.

DETAILED DESCRIPTION

Figure 1:
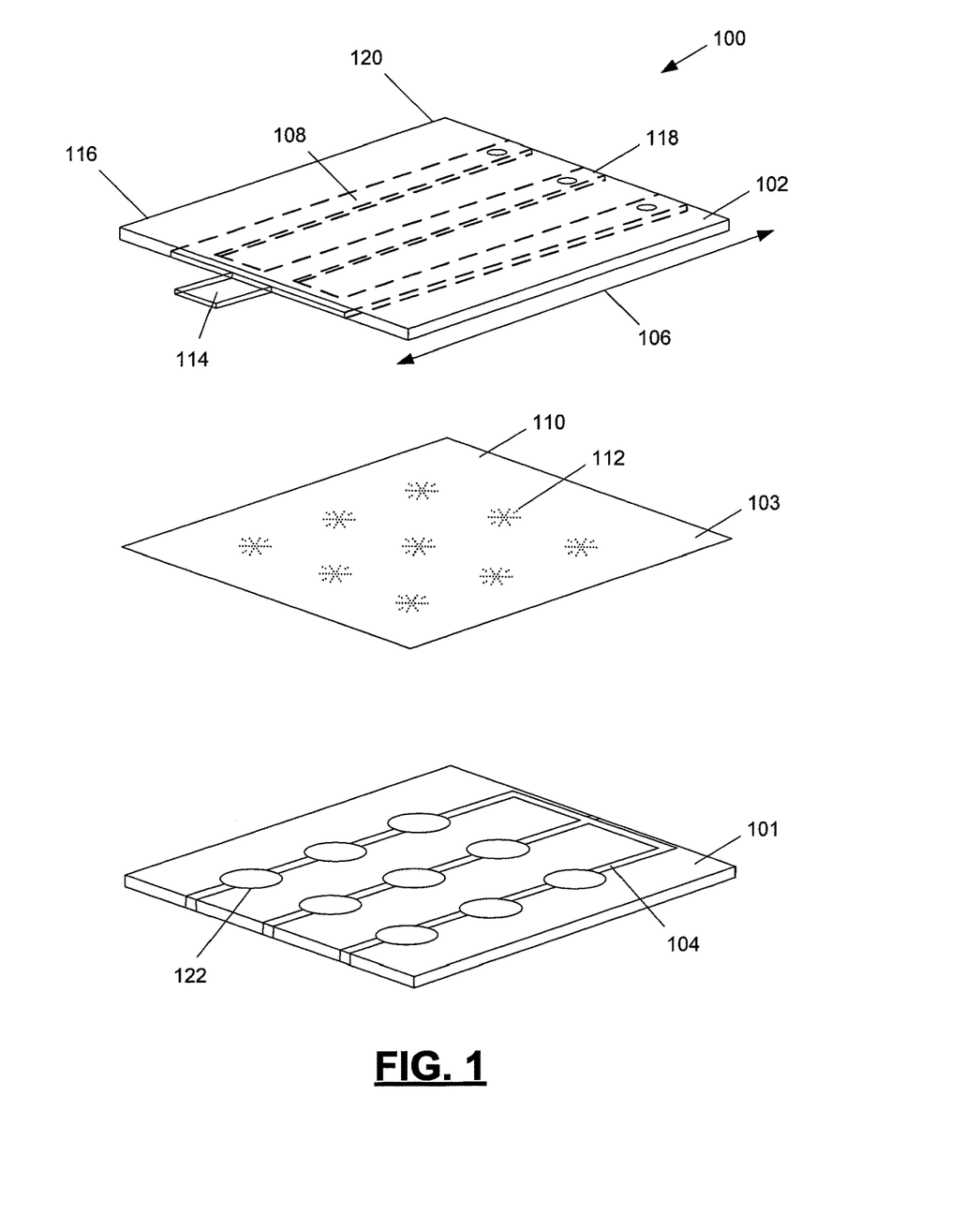
FIG. 1 is an exploded view of an exemplary cell array.

FIG. 1, is an exploded view of an exemplary layered three-dimensional (3D) microfluidic living cell array 100. The cell array 100 provides a nanoscaffold hydrogel that permits cells, such as cloned cancer or nonmalignant cells, to grow in a synthetic three-dimensional matrix. Cell array 100 comprises a first layer 101, a second layer 102 and a third layer 103 that is disposed between the first layer 101 and the second layer 102. In the embodiment depicted, the third layer 103 is in contact with both the first layer 101 and the second layer 102. The first layer 101 comprises a plurality of cell culture channels 104 which, in the exemplary embodiment, includes a plurality of cell culture chambers 122. The third layer 103 comprises a filter membrane 110 with a nest of pores 112 that fluidly connect a cell culture channel 104 to a microfluidic channel 108 of the second layer 102. The microfluidic channel 108 extends along longitudinal direction 106. The microfluidic channel 108 comprises a fluid inlet 114 at a first end 116 of the second layer 102 and a fluid outlet 118 at a second end 120 of the second layer 102. The first end 116 and the second end 120 are disposed on opposite ends of the second layer 102 and are spaced apart along longitudinal direction 106. The fluid inlet 114 may be connected to, for example, a syringe pump for delivering fluids at a predetermined flow rate. The flow rate may be selected to approximate the flow rate of blood through a small blood vessel. In one embodiment, the flow velocity is between 500-1000 microns per second. In another embodiment, the flow rate is between 100-800 microns per second. In yet another embodiment the flow rate is between 100-200 microns per second. The flow rate is the product of the flow velocity multiplied by the cross-sectional area of the channel.

Figure 2:
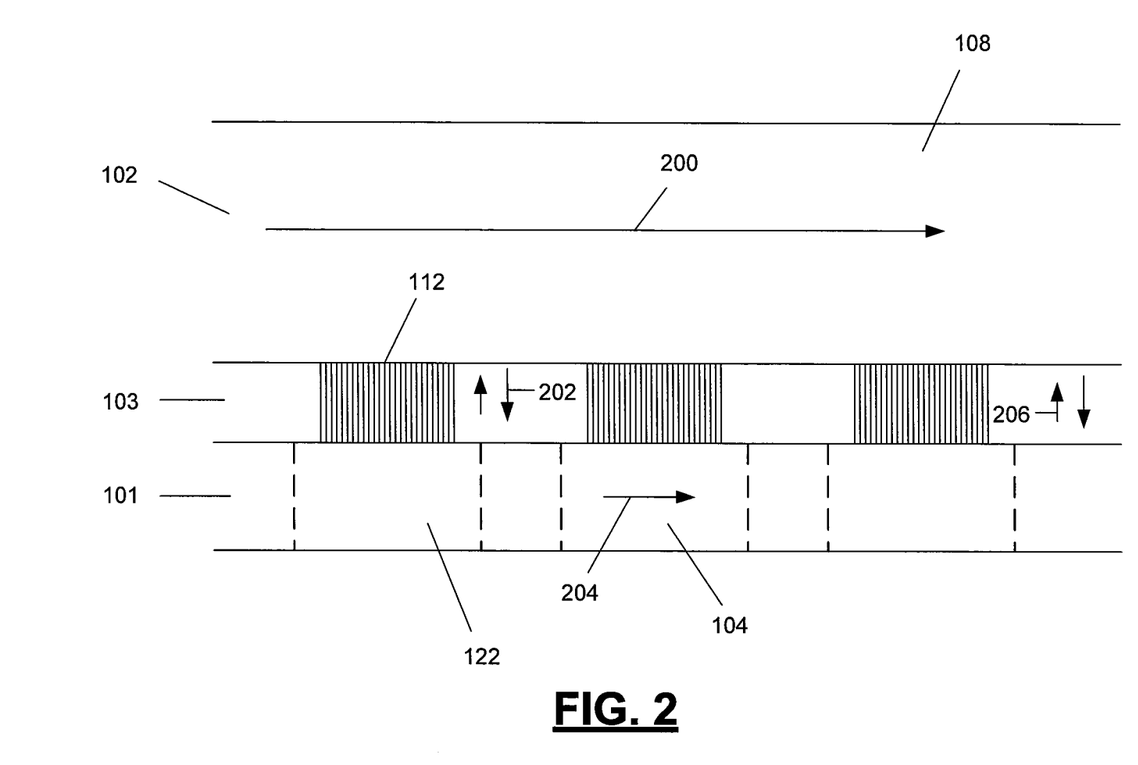
FIG. 2 is a bisected profile of an exemplary cell array.

Referring to FIG. 2, during operation cells are introduced into the cell culture channels 104 (e.g. introduced into the cell culture chambers 122). The cell culture channels 104 may be filled with a suitable media, such as a hydrogel media. The media provides a porous environment suitable for growing cells. Nutrients are dissolved or suspended in a liquid and introduced into the fluid inlet 114 at a predetermined rate. The fluid flows in direction of arrow 200 until it exits the fluid outlet 118. The flow rate through microfluidic channel 108 flows at a relatively high rate, compared to the very low flow rate through the second layer 102 and the low flow rate in the third layer 103. Advantageously this minimizes the shear stress cells experience in the cell array to more closely approximate an in vivo environment.

As shown in FIG. 2, a nest of pores 112 fluidly connect the microfluidic channel 108 to the cell culture channels 104. In the embodiment depicted, each of nest of pores 112 are arranged such that they are vertically stacked above a corresponding cell culture chamber 122 of the cell culture channel 104. Nutrients in the fluid pass into the cell culture channels 104 in the direction of arrow 202, limited by the size of the pores within the nest of pores 112. This is generally a diffusion-controlled process. Once the nutrients pass into the cell culture channels 104 they are transported in the direction of arrow 204. Other material, such as the waste products of the cells and excess nutrients, diffuse in the direction of arrow 206 where they rejoin the fluid in the microfluidic channel 108. These other materials are transported in the direction of arrow 200 where they exit cell array 100 at fluid outlet 118.

Figure 3A:
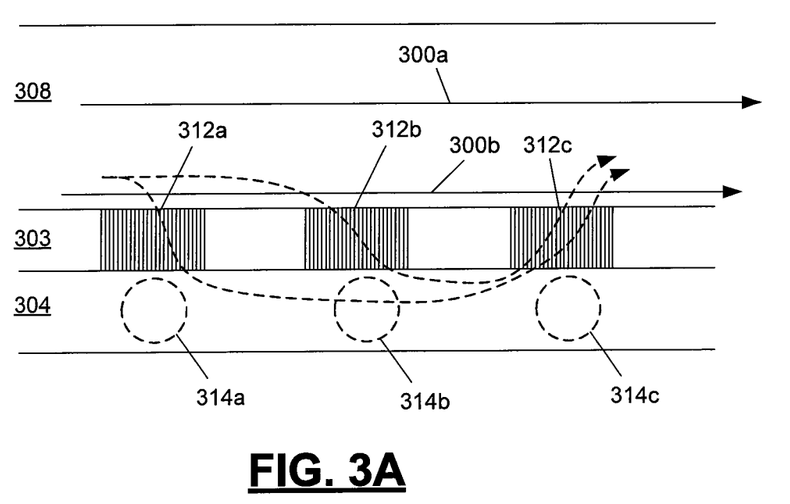

The microfluidic dynamics of cell array 100 provides a three dimensional environment that closely approximates the environment experienced by a cell in its native (biological) environment. By mimicking the fluid dynamics provided by arteriole, venule and capillary systems, cells grown within the cell array 100 can be grown in a fashion that more closely matches native growth patterns. This makes it more likely the cloned cells will retain the biological characteristics (e.g. drug susceptibility) of the cells, leading to more accurate drug screening tests. FIG. 3A provides another view of the microfluidic dynamics of cell array 100.

FIG. 3A shows a microfluidic channel 308, a third layer 303 with pores 312a, 312b and 312c. A cell culture channel 304 is also depicted. Fluid flows quickly through the microfluidic channel 308 in the direction of arrow 300a. Due to fluid dynamics, the flow rate of the fluid proximate the walls of the microfluidic channel 308 is slower. See arrow 300b. A portion of the fluid passes through nest of pores 312a, 312b and 312c, into the cell culture channel 304 and exits the pores to rejoin the microfluidic channel 308. Fluid dynamic calculations indicate the flow rate in the cell culture channel 304 is, in one embodiment, about 0.1 micrometers per second, which corresponds to the interstitial flow rate in vivo. Wherein a cell culture channel, flow rate through the nest of pores 312a (the upstream pore) is relatively fast. Likewise, the flow rate through nest of pores 312c (the downstream pore) is also relatively fast. The flow rate through nest of pores 312b, which is between the upstream and downstream pore, is somewhat slower. The flow rate gradually changes with the nest of pores at the center of the third layer 303 having the slowest flow rate. The flow rate through the nest of pores increases as one moves either upstream or downstream relative to the central nest.

The flow rate through the cell culture channel 304 is generally fastest at point 314b which is at the center of the cell culture channel 304. The flow rates through cell culture channel 304 decreases as one moves either upstream or downstream from the center of the cell culture channel 304. For example, fluid dynamic calculations show the flow rates at points 314a and 314b are relatively slow. The fluid dynamic behavior results in a subtle concentration gradient of material within the fluid. Examples of two such gradients are shown in FIG. 3B.

Figure 3B:
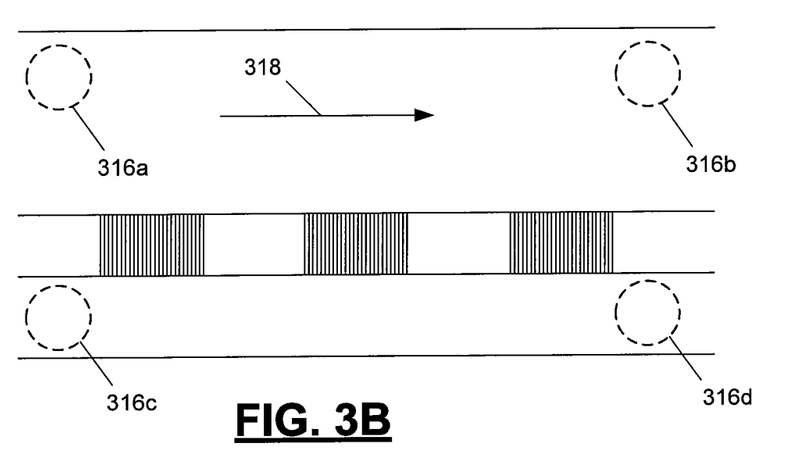
FIG. 3B is a bisected profile of an exemplary cell array showing concentration gradients.

FIG. 3B schematically depicts the subtle concentration gradients for a nutrient (oxygen) and a waste product (carbon dioxide). The subtle concentration gradient confirms that the cell array can efficiently perform oxygen delivery and carbon dioxide removal even with subtle concentration gradients. The concentration of oxygen is relatively high at point 316a. As the fluid flows in the direction of arrow 318, a portion of the oxygen migrates through the pores and is consumed by the cells. The concentration of oxygen at point 316b is therefore lower than point 316a. Modeling suggests the concentration gradient in the microchambers is present, but subtle (e.g. about 0.0003%) and that the vertical concentration gradient between the first layer and the second layer is sufficient for efficiency oxygen/carbon dioxide exchange. The lowest concentration of oxygen is at point 316d. The concentration of oxygen at point 316c is similar to that of point 316b, due to a balancing of diffusion and flow rate. In a similar fashion, the concentration of carbon dioxide follows the same trend with the opposite direction. Carbon dioxide concentration is relatively low at point 316a. As the fluid flows in the direction of arrow 318, a portion of the carbon dioxide migrates from the cells through the pores and joins the fluid. The concentration of carbon dioxide at point 316b is therefore higher than point 316a. The highest concentration of carbon dioxide is at point 316d. The concentration of carbon dioxide at point 316c is similar to that of point 316b, due to a balancing of diffusion and flow rate.

Figure 4:
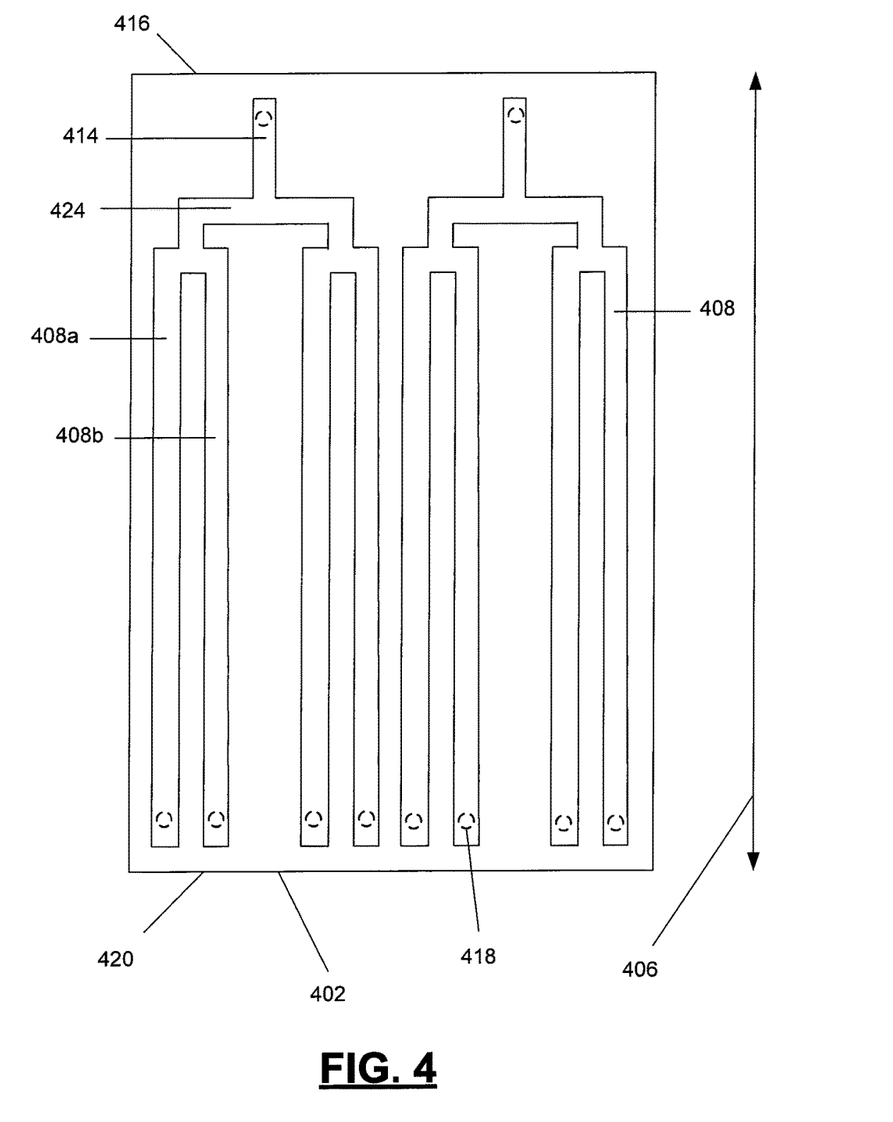
FIG. 4 is a schematic view of an exemplary second layer.

FIG. 4 is a detailed top view of an exemplary second layer 402. The second layer 402 is formed of an optically transparent material to facilitate viewing of the cellular samples as well as probing of the samples using microscopic techniques. The second layer 402 comprises a plurality of microfluidic channels 408 including a first microfluidic channel 408a and a second microfluidic channel 408b. The channels extend in a longitudinal direction 406. The first microfluidic channel 408a and the second microfluidic channel 408b are fluidly connected by a joining channel 424 at a first end 416 which is opposite second end 420. When fluid is introduced to fluid inlet 414, the fluid flows through joining channel 424 and into the first microfluidic channel 408a and the second microfluidic channel 408b. Excess fluid exits through fluid outlet 418. The microfluidic channels 408 are vertically stacked above the pores of the third layer 503. See FIG. 5.

Figure 5:
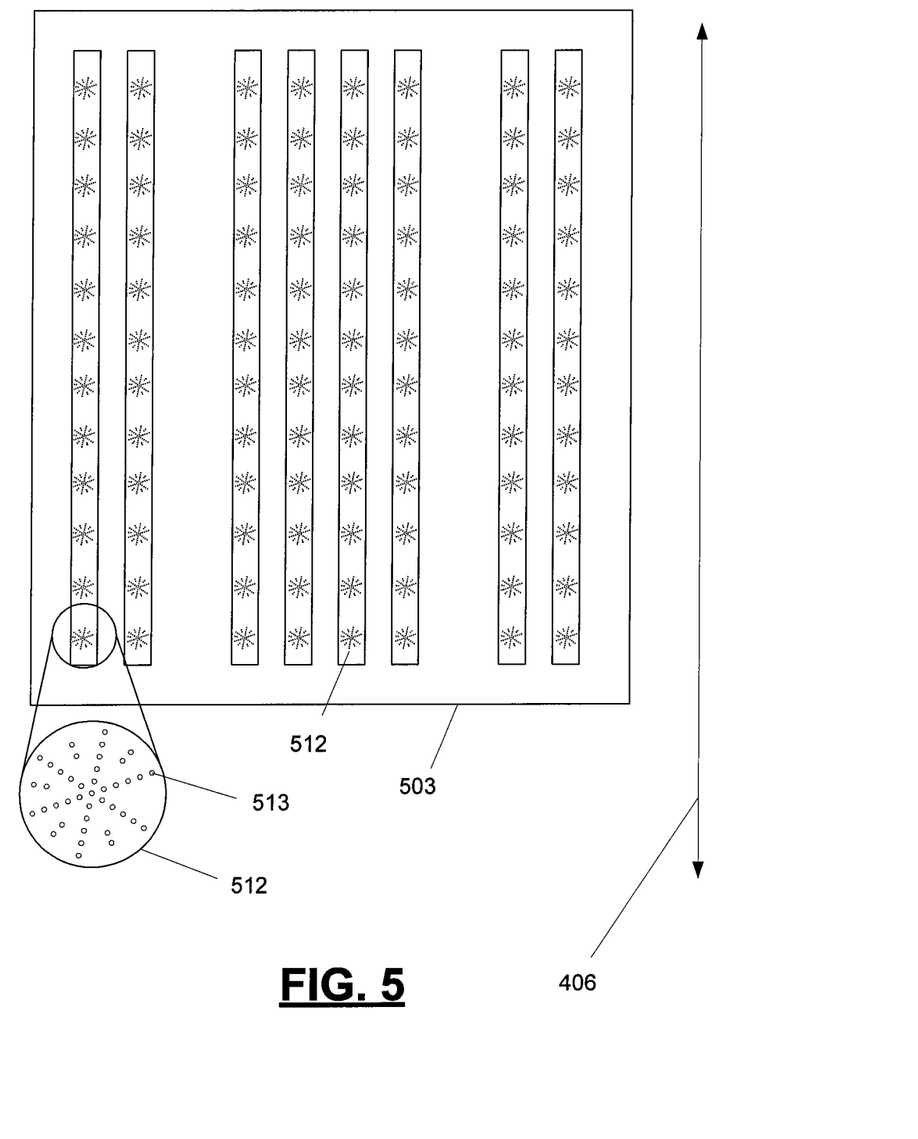
FIG. 5 is a schematic view of an exemplary third layer.

FIG. 5 is a depiction of an exemplary third layer 503. The third layer 503 is formed of an optically transparent material. In the embodiment of FIG. 5, the pores 513 are grouped into nests of pores 512. The pores 513 have a diameter suitable to control the rate of diffusion of material through the pores. The pores 513 may have a diameter of between about 10 micrometers and about 40 micrometers. For example, in one embodiment the pores 513 have a diameter of about 20 micrometers. The nests of pores 512 are arranged in a line that extends along longitudinal direction 406 so as to vertically stack the pores 513 with the microfluidic channels 408 and fluidly connect them. The nests of pores 512 are also arranged to be vertically stacked above corresponding cell culture chambers. In one embodiment, there is one nest of pores 512 for each cell culture chamber (i.e. a one-to-one ratio).

Figure 6:
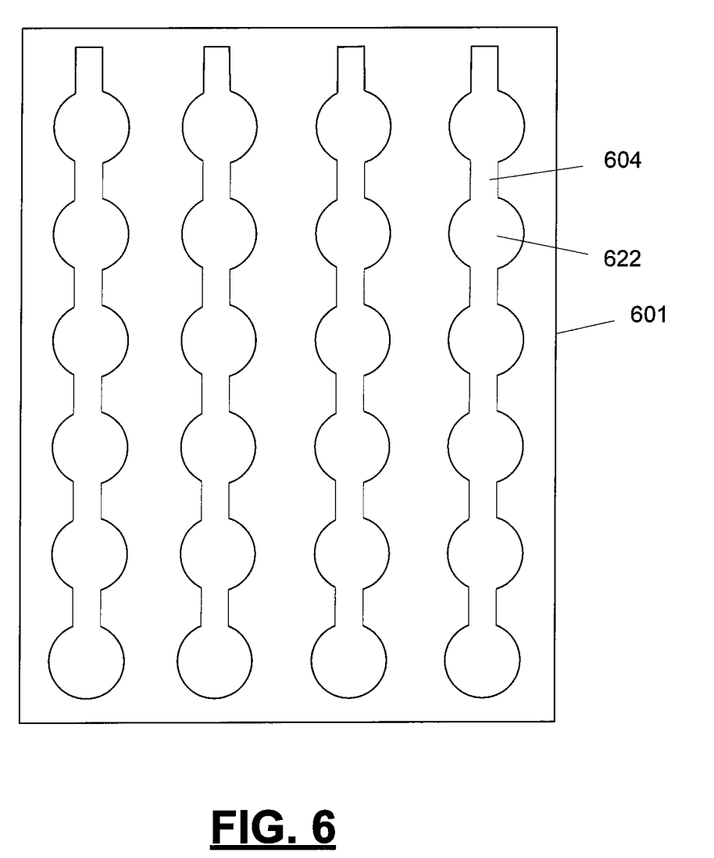
FIG. 6 is a schematic view of an exemplary first layer.
Figure 7:
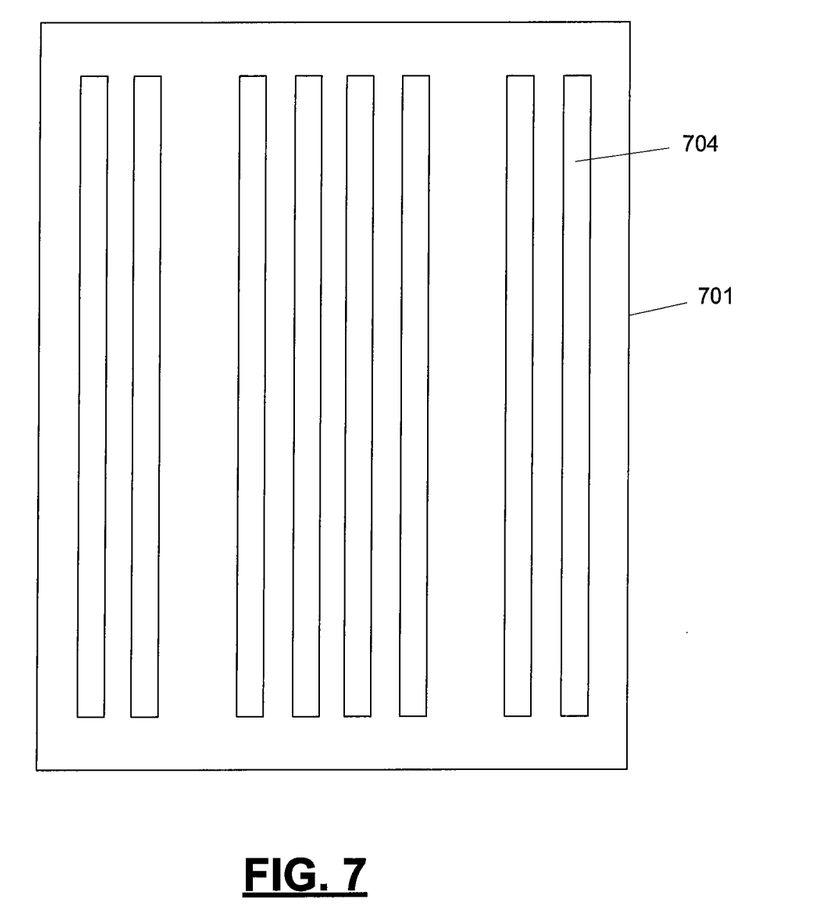
FIG. 7 is a schematic view of an exemplary first layer.

FIG. 6 is a top view of an exemplary first layer 601. The first layer 601 is formed of an optically transparent material. The first layer 601 comprises a plurality of cell culture chambers 622 joined by cell culture channels 604. In the embodiment depicted there are twenty-four cell culture chambers 622 in a 4×6 array of cell culture chambers. Such an embodiment may be used with a third layer that has twenty-four nests of pores, each of which is vertically stacked above a corresponding cell culture chamber. A wide variety of cell culture chamber configurations may be used. For example, an 8×8 array of cell culture chambers may be used. In another embodiment, a 10×10 array is used. The aforementioned arrays and merely examples. The cell array is highly scalable for use in high throughput drug screen in a clinical or industrial setting. In those depicted embodiments where cell culture chambers are used, the chambers are circles with a diameter greater than the width of the cell culture channels. In one embodiment, the cell culture chambers are circles with a diameter between about 100 micrometers and about 800 micrometers. In one embodiment, the cell culture chambers are circles with a diameter of about 770 micrometers. The width of the cell culture channels and the microfluidic channels corresponds to the width of blood vessels and is generally several hundred micrometers. This precise width may be adjusted depending on what types of blood vessels are being mimicked. In one embodiment, the width of the channels is between 50 microns and 500 microns. In another embodiment, shown in FIG. 7, the first layer 701 comprises a plurality of cell culture channels 704 that do not include designated cell culture chambers 122. Cellular growth occurs within cell culture channels 704.

Figure 8:
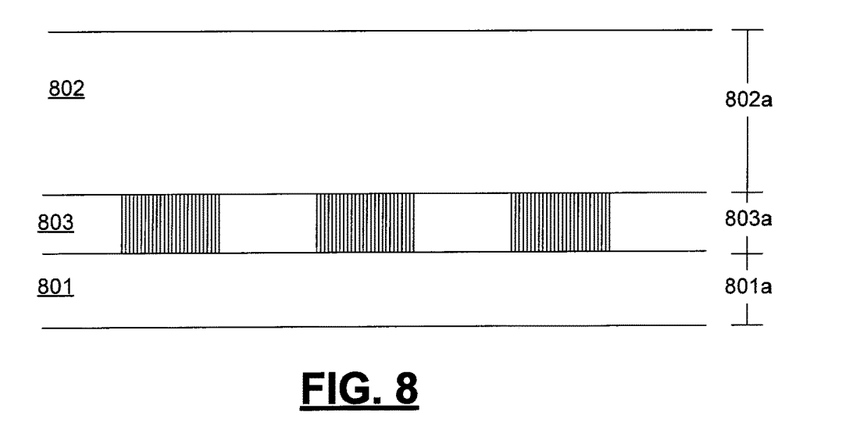
FIG. 8 is a bisected profile of an exemplary cell array.

FIG. 8 is a bisected side view of an exemplary cell array 800 comprising first layer 801, second layer 802 and third layer 803. The first layer 801 has a first thickness 801a. The second layer 802 has a second thickness 802b. The third layer 803 has a third thickness 803a. In the embodiment depicted, the first thickness 801a is greater than the third thickness 803a but is less than the second thickness 802a. In one embodiment, the first thickness 801 a is between 60 and 100 micrometers. In another embodiment, the first thickness 801a is between 70 and 90 micrometers. In one embodiment, the second thickness 802a is about 130 micrometers, the third thickness 803a is about 40 micrometers and the first thickness 801a is about 80 micrometers. By providing a relatively thick second layer 802, a desirable flow rate is maintained. By controlling the thickness of third layer 803, the diffusion rate can be controlled. The thickness of the first layer 801 provides a three-dimensional volume within which cells can be grown. The relative thickness of first layer 801 impacts the microfluidics of the cell array.

Figure 9:
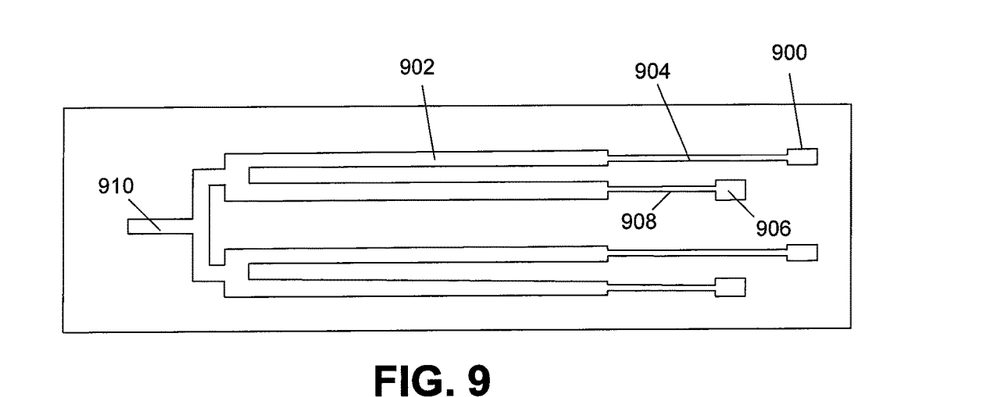
FIG. 9 is a schematic view of a channel with access ports.

In some embodiments, a first access port 900 is disposed at a terminus of a channel 902 that connects the channel 902 to the ambient environment. Fluid, which may contain samples, may be withdrawn through these access ports. Channel 902 may be a cell culture channel of the first layer or a microfluidic channel of the second layer. In those embodiments where the channel 902 is a microfluidic channel of the second layer, the access port can function as a fluid outlet where excess liquid is expelled. In those embodiments where the channel 902 is a cell culture channel, the access port can be used to selectively withdraw samples for subsequent testing. To access the content of channel 902, one can form (as by drilling) a hole in the layer. Since the first access port 900 has a relatively large area, it is easier to properly position the hole than it would be were first access port 900 small. This is particularly advantageous considering the small size of many of the exemplary arrays. To avoid inadvertently drilling into channel 902, the first access port 900 is spaced from the channel 902 by a path 904 that fluidly connects the access port 900 to the channel 902. To minimize the volume of fluid that occupies the path 904, the width of path 904 is narrower than the width of channel 902. When a second access port 906 is proximate the first access port 900, it can be difficult to drill a hole to access one port without inadvertently drilling into the other access port. To minimize this risk, second access port 906 is staggered relatively to the first access port 900 by utilizing a second path 908 which has a length different from the length of path 904. In the embodiment depicted, path 908 is shorter than path 904. In a similar fashion, one can access fluid inlet 910 by drilling a hole in the layer to expose the fluid inlet 910 to the ambient environment.

In one embodiment, the first, second and third layers are formed of an optically transparent material to facilitate visual inspection of the cells as well as permit microscopic probing of the sample. Examples of suitable materials include polydimethylsiloxane (PDMS) and other similar materials.

In one embodiment, the hydrogel is a peptide-based hydrogel sold under the brand name PURAMATRIX™. This hydrogel is an exemplary peptide-based hydrogel with over 99% water content that can self-assembly into 3D interweaving nanofibers after a salt solution is added. Such a hydrogel provides pore size ranges from about 50 nm to about 200 nm. The peptide sequence may be chosen to promote cell attachment and migration (e.g. peptide RAD16-I).

In the embodiments depicted, a select number of channels are shown. It should be understood that other embodiments may use more channels or fewer channels and that such embodiments are contemplated for use with the present invention. Additionally, the fluid inlets and fluid outlets are exchangeable. This permits a different number of drugs to be introduced. For example, two inlets may be used with eight outlets when two drugs are employed. As a further example, eight inlets with two outlets may be used when eight drugs are employed. The fluid inlets and fluid outlets are not necessarily at opposite ends of the cell array. Depending on the fluid pathway, the fluid inlet and/or fluid outlet may be positioned at another location.

An imaging method to detect dynamic signals from live cells cultured in the cellular array is may be used to monitor cell growth in real time. For example, fluorescence microscopy and z-direction slicing with a moving objective and an on-stage incubator may be used. Suitable equipment is commercially available and includes the AxioObserver Z1 by Zeiss, Inc. Deconvolution software may be used to generate clear 3D cell images from z-stack images. The system described herein permits real time drug mechanism studies, including drug kinetics with spatial resolutions in apoptotic signaling networks using a scalable 3D microfluidic platform.

Figure 10:
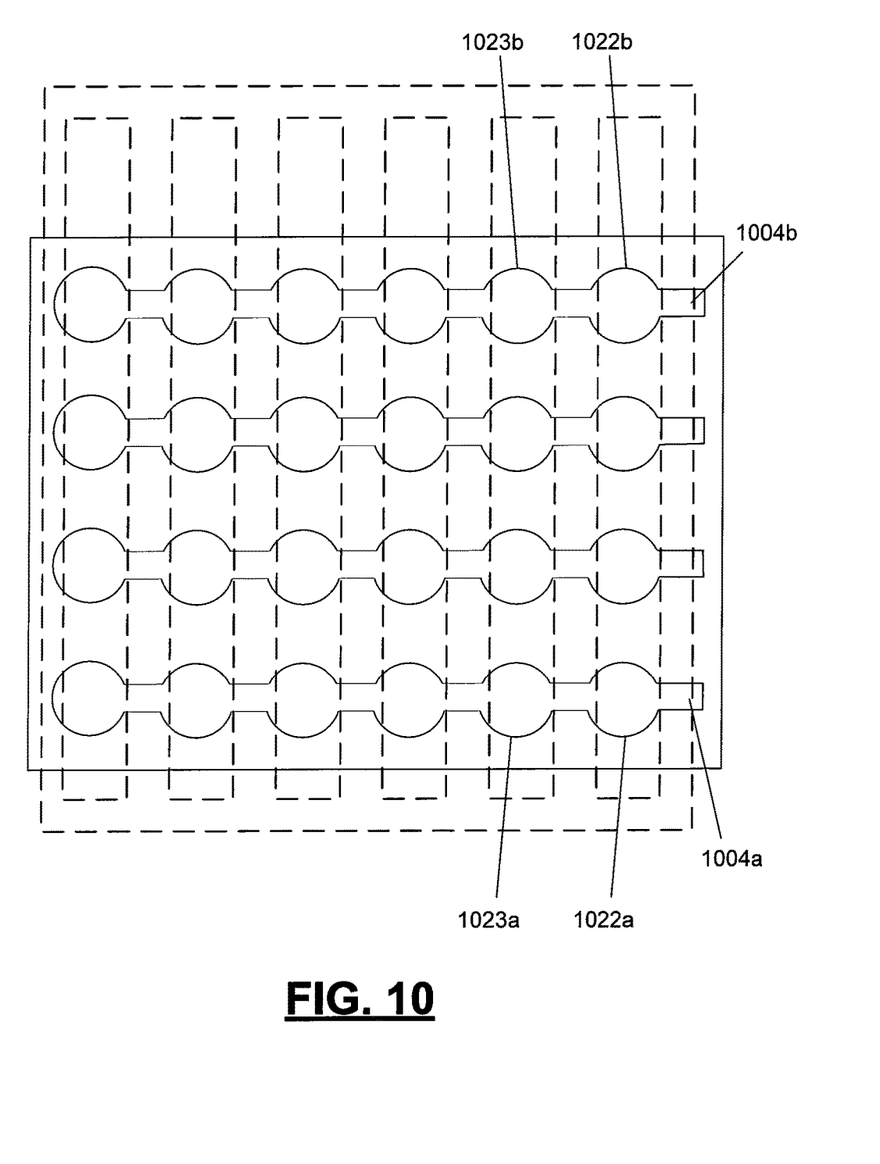
FIG. 10 is a schematic view of an exemplary first layer used in a combinatorial drug screening process.

Referring to FIG. 10, in one embodiment, the cell array is used in a combinatorial drug screening process. A variety of cellular samples may be placed in a cell array in which each sample is disposed in its own cell culture chamber to form rows. For example, a first type of cancer cell may be placed in first cell culture chambers 1022a, 1023a while a second type of cancer cell is placed in second cell culture chambers 1022b, 1023b. A select drug is screened by sending the drug, at a predetermined concentration, through a microfluidic channel. For example, a first drug is introduced into the array such that it contacts cell culture channel 1004a while a second drug is introduced into the array such that it contacts cell culture channel 1004b. In the embodiment of FIG. 10, the first layer and the second layer are orthogonal with the second layer shown in phantom. Because the rows of cancer cell types are orthogonal to the longitudinal direction of the cell culture channels, a wide variety of drugs can be screened against multiple cancer cell types. In one embodiment, microvalves are positioned in the cell culture channel between each of the cell culture chambers. The microvalves prevent two different drugs from cross contaminating the cell culture chambers. Suitable microvalves are known. See, for example, an article entitled "A high-throughput microfluidic real-time gene expression living cell array" by King et al. (Lab Chip; 2007 January; 7(1) 77-75). When the bottom layer is seeded with cells, the valves may be opened. After seeding, the valves may be closed. One of the microfluidic channels may be a drug-free fluid to function as a control.

One advantage of the technique described above is the ability of the system to microscopically monitor cell growth in real time as the cell culture develops. In one embodiment, the microscopic data is subjected to data mining to permit the screening process to be automated. Another advantage is the capability of using the cell array in personalized medicine. Tumor cells, and/or other types of cells, from a particular patient may be quickly subjected to a wide variety of drugs so that the most effective drug for that individual can be quickly identified.

The layers described in this specification may be formed according to conventional microfabrication techniques. Such techniques are employed in the field of micro-electromechanical systems (MEMS). For example, a silicon wafer may be coated with a layer of photoresist. A patterned mask is used to selectively protect those areas of the wafer which will be the channels or pores. Treatment with ultraviolet light etches those areas not protected by the mask to produce a master mold. The master mold is coated with a polymerizable mixture. Upon polymerization, the layers are formed with the appropriate patters or pores and separated from the mold.

While the invention has been described with reference to certain embodiments, it will be understood by those skilled in the art that various changes may be made and equivalents may be substituted for elements thereof to adapt to particular situations without departing from the scope of the disclosure. Therefore, it is intended that the claims not be limited to the particular embodiments disclosed, but that the claims will include all embodiments falling within the scope and spirit of the appended claims.

EXAMPLE 1

The device was tested by using food dyes. Liquid food dyes were introduced to the fluid inlets of the second layer with syringes. The flow with food colors moved through microfluidic channels and at the same time the dye diffused from the second layer to the first layer by passing through the pores on the third layer in 2.5 seconds. The diffusion time was estimated using a video capturing the complete procedure of the food color experiment.

EXAMPLE 2

PC9 (non-small lung cancer) cells encapsulated in peptide hydrogel were cultured in the first layer for seven days. On day seven, calcein AM was introduced in the second layer to test the diffusion of the dye and viability of the cells. Live cells should be fluorescent green. Microscopic inspection showed that diffusion of calcein AM happens in seconds, and by fifty-two seconds all live cells become fluorescent green.

EXAMPLE 3

A long term 3D cell culture for two weeks was also performed. PC9 cells were dyed with long term green fluorescent cell tracker and encapsulated in peptide hydrogel. A syringe pump was used to deliver fresh medium continuously at 0.5 microliters per minute in the second layer. Cells were imaged using an 10× objective with z-direction moving ability. Then a 3D image was reconstructed using z-stack images after deconvolution showing live cells.

EXAMPLE 4

In order to show our device is feasible to perform a structured co-culture between cancer cells and endothelial cells, PC9 were dyed with red fluorescence cell tracker (DIL), seeded and cultured in the first layer for several days, followed by microvascular endothelial cell seeding in the second layer without dye. Microscopic inspection showed that a structured co-culture was achieved successfully. This experiment confirmed that not only micro-tumor arrays can be generated but that tumor microenvironments can also be mimicked that are similar to their in vivo conditions (e.g. tumors are surrounded by blood vessels without lymph vessels).

What is claimed is:
1. A layered, microfluidic living cell array, comprising:
   a first layer comprising a plurality of cell culture channels extending in a longitudinal direction, wherein each of the cell culture channels further comprises a plurality of cell culture chambers that are fluidly connected by the corresponding cell culture channel, each of the cell culture chambers being circular with a diameter of 100 micrometers to 800 micrometers, wherein the first layer is formed of an optically transparent material;
   a second layer comprising a plurality of microfluidic channels including a first channel and a second channel, wherein the plurality of microfluidic channels extend in a longitudinal direction, and wherein the first channel and the second channel are fluidly connected by a joining channel at a first end which is opposite a second end;
   a third layer, disposed between the first layer and the second layer, the third layer comprising a membrane with a plurality of pores extending in a longitudinal direction, each pore having a diameter of 10 micrometers to 40 micrometers, each pore fluidly connecting the plurality of microfluidic channels of the second layer to the plurality of cell culture channels of the first layer, wherein each pore is grouped into nests of pores, each nest in the nests of pores being vertically stacked above a corresponding cell culture chamber in the plurality of cell culture chambers such that each nest in the nests of pores is within an area defined by a circumference of the corresponding cell culture chamber, and each nest being within the plurality of cell culture channels, wherein each nest in the nests of pores is spaced from adjacent nests by fluid impermeable regions of the third layer that fluidly isolate each nest from adjacent nests such that diffusion of fluids between each nest and adjacent nests through the third layer is prevented, thereby preventing cross-contamination between the first channel and the second channel;

a fluid inlet connected to the first end;

a fluid outlet connected to the second end, wherein the ratio of nests of pores to the plurality of cell culture chambers is a one-to-one ratio.

2. The layered, microfluidic living cell array as recited in claim 1, wherein the plurality of microfluidic channels have a width between 50 micrometers and 500 micrometers.

3. The layered, microfluidic living cell array as recited in claim 1, wherein the first layer, the second layer and the third layer are formed of an optically transparent material.

4. The layered, microfluidic living cell array as recited in claim 3, wherein the first layer, the second layer and the third layer are formed of polydimethylsiloxane (PDMS).

5. The layered, microfluidic living cell array as recited in claim 1, wherein the plurality of cell culture channels contains a hydrogel.

6. The layered, microfluidic living cell array as recited in claim 1, wherein the first layer has a first thickness, the second layer has a second thickness, and the third layer has a third thickness, the first thickness being greater than the third thickness but is less than the second thickness.

7. The layered, microfluidic living cell array as recited in claim 6, wherein the first thickness is between 60 micrometers and 100 micrometers and the first thickness is greater than the third thickness but is less than the second thickness.

8. The layered, microfluidic living cell array as recited in claim 1, further comprising a first access port disposed at the second end of the first channel.

9. The layered, microfluidic living cell array as recited in claim 8, further comprising a first path fluidly connecting the first channel to the first access port, the first path having a first width that is less than a width of the first channel.

10. The layered, microfluidic living cell array as recited in claim 9, further comprising a second access port disposed at the second end of the second channel the layered, microfluidic living cell array further comprising a second path fluidly connecting the second channel to the second access port, the second path having second width that is less than a width of the second channel, the first path having a first length and the second path having a second length, the first length and second length being different so as to stagger the first access port and the second access port.

11. The layered, microfluidic living cell array as recited in claim 1, wherein the plurality of cell culture channels and the plurality of microfluidic channels are orthogonal.

12. The layered, microfluidic living cell array as recited in claim 1, wherein the plurality of cell culture channels and the plurality of microfluidic channels are parallel.

* * * * *